United States Patent
Greenwald et al.

(10) Patent No.: US 6,756,037 B2
(45) Date of Patent: Jun. 29, 2004

(54) POLYMER CONJUGATES OF BIOLOGICALLY ACTIVE AGENTS AND EXTENSION MOIETIES FOR FACILITATING CONJUGATION OF BIOLOGICALLY ACTIVE AGENTS TO POLYMERIC TERMINAL GROUPS

(75) Inventors: Richard B. Greenwald, Somerset, NJ (US); Yun H. Choe, Green Brook, NJ (US)

(73) Assignee: Enzon, Inc., Piscataway, NJ (US)

( * ) Notice: Subject to any disclaimer, the term of this patent is extended or adjusted under 35 U.S.C. 154(b) by 94 days.

(21) Appl. No.: 09/823,283

(22) Filed: Mar. 29, 2001

(65) Prior Publication Data

US 2001/0051144 A1 Dec. 13, 2001

Related U.S. Application Data

(60) Provisional application No. 60/193,726, filed on Mar. 31, 2000.

(51) Int. Cl.[7] .................... A61K 39/395; A61K 39/385; A61K 9/127
(52) U.S. Cl. ................. 424/178.1; 424/179.1; 424/194.1; 424/181.1; 424/450; 424/180.1
(58) Field of Search .......................... 424/178.1, 179.1, 424/194.1, 181.1, 450, 180.1

(56) References Cited

U.S. PATENT DOCUMENTS

| 5,283,339 | A |   | 2/1994  | Arnold et al. ............... 548/104 |
| 5,382,657 | A |   | 1/1995  | Karasiewicz et al. ....... 530/351 |
| 5,433,886 | A |   | 7/1995  | Sherbondy et al. ......... 252/180 |
| 5,454,954 | A |   | 10/1995 | Alfano et al. ............... 210/700 |
| 5,583,206 | A |   | 12/1996 | Snow et al. .................. 534/16 |
| 5,620,689 | A | * | 4/1997  | Allen et al. ............... 424/178.1 |
| 5,643,575 | A |   | 7/1997  | Martinez et al. .......... 424/194.1 |
| 5,646,159 | A |   | 7/1997  | Wall et al. ................... 514/279 |
| 5,679,852 | A |   | 10/1997 | Platzek et al. .............. 564/138 |
| 5,693,310 | A |   | 12/1997 | Gries et al. .............. 424/9.365 |
| 5,693,626 | A |   | 12/1997 | Saksena et al. ............... 514/85 |
| 5,756,825 | A |   | 5/1998  | Safavy et al. ............... 560/169 |

(List continued on next page.)

FOREIGN PATENT DOCUMENTS

| EP | 0 809 996 A2 | 3/1997 |
| WO | WO 95/09883 | 4/1995 |

OTHER PUBLICATIONS

Benaglia, M., et al., Synthesis of New Poly(ethyleneglycol)s with a High Loading Capacity, J. Org. Chem., 1998, pp. 8628–8629.

(List continued on next page.)

*Primary Examiner*—Jezia Riley
(74) *Attorney, Agent, or Firm*—Muserlian, Lucas & Mercanti, LLP

(57) ABSTRACT

The present invention is directed to polymer conjugates of biologically active agents and methods of preparing the same. In preferred aspects of the invention, the conjugates are of the formula

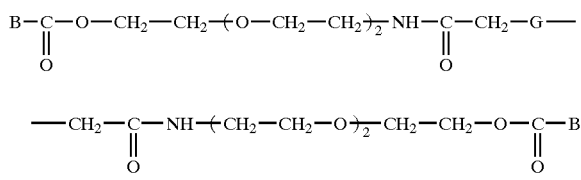

wherein G is a linear or branched polymer residue such as a polyethylene glycol and B is a residue of an amine-containing or a hydroxyl-containing biologically active moiety such as Ara-C.

32 Claims, 3 Drawing Sheets

U.S. PATENT DOCUMENTS

| | | | |
|---|---|---|---|
| 5,919,455 A | 7/1999 | Greenwald et al. | 424/178.1 |
| 5,932,462 A | 8/1999 | Harris et al. | 435/188 |
| 5,968,943 A | 10/1999 | Cao et al. | 514/283 |
| 5,994,517 A | 11/1999 | Ts'o et al. | 530/391.9 |
| 6,020,373 A | 2/2000 | Schellenberg et al. | 514/547 |
| 6,039,931 A | 3/2000 | Schmitt-Willich et al. | 424/9.364 |
| 6,113,906 A | 9/2000 | Greenwald et al. | 424/194.1 |

OTHER PUBLICATIONS

Chen, J., et al., Thiol–Reactive Luminescent Chelates of Terbium and Europium, Bioconjugate Chem., 1999, pp. 311–315.

King, H.D., et al., Monoclonal Antibody Conjugates of Doxorubicin Prepared with Branched Linkers: A Novel Method for Increasing the Potency of Doxorubicin Immunoconjugates, Bioconjugate Chem., 1999, pp. 279–288.

Ohya, Y., et al., Synthesis and Cytotoxic Activity of Conjugates of Monomethoxy–Poly-(ethylene glycol) End–capped with Doxorubicin via Ester, Amide, or Schiff's Base Bond, Journal of Bioactive and Compatible Polymers, 1995, pp. 51–66.

Hines, J.V., et al., Paramagnetic Oligonucleotides: Contrast Agents for Magnetic Resonance Imaging with Proton Relaxation Enhancement Effects, Bioconjugate Chem., Mar./Apr. 1999, vol. 10, No. 2, pp. 155–158.

Yamasaki, N., et al., Some Properties of Ricin D Modified with a Methoxypolyethylene Glycol Derivative, Agric. Biol. Chem., 1990, vol. 54, No. 10, pp. 2635–2640.

Greenwald, R.B., et al., Drug Delivery Systems Employing 1,4– or 1,6– Elimination: Poly (ethylene glycol) Prodrugs of Amine–Containing Compounds, Journal of Medicinal Chemistry, 1999, vol. 42, No. 18, pp. 3657–3667.

Shearwater Polymers Catalog, Inc., Group Three A—Active Esters, p. 13, 2000.

Greenwald, R.B., et al. ,Poly(ethylene glycol) Conjugated Drugs and Prodrugs: A Comprehensive Review, Critical Reviews in Therapeutic Drug Carrier Systems, 2000, vol. 17, No. 2, pp. 101–161.

Williams, M.A., et al., Synthesis of Enantiomerically Pure Diethylenetriaminepentaacetic Acid Analogues. L–Phenylalanine as the Educt for Sunstituion at the Central Acetic Acid, J. Org. Chem., 1993, vol. 58, pp. 1151–1158.

Shearwater Polymers, Inc. Catalog, Polyethylene Glycol Derivatives, Star Pegs and Branched Pegs, 1997–1998, p. 8.

Shearwater Polymers, Inc., Quaterly Newsletter, Mar. 1998, No. 1.

Saksena, Anil K., et al., Concise Asymmetric Routes to 2,2,4–Trisubstituted Tetrahydrofurans Via Chiral Titanium Imide Enolates: Key Intermediates Towards Synthesis of Highly Active Azole Antifungals SCH 510–18 and SCH 56592, Tetrahedron Letters, vol. 37, No. 32, pp. 5657–5660, 1996.

Twyman, L.J. , et al., The Synthesis of Water Soluble Dendrimers, and their Application as Possible Drug Delivery Systems, Tetrahedron Letters, vol. 40, 1999, pp. 1743–1746.

Cerny, L.C., et al., A Potential Blood Substitute From a Tetronic Polyol And A Modified Hemoglobin, Biomat., Art. Cells & Immob. Biotech., vol. 20, No. 1, pp. 71–93, 1992.

Greenwald, R.B., Oncologic, Endocrine & Metabolic: Drug Delivery Systems: Anticancer Prodrugs and their Polymeric Conjugates, Exp. Opin. Ther. Patents, vol. 7, No. 6, pp. 601–609, 1997.

Monfardini, C., et al., A Branched Monomethoxypoly(ethylene glycol) for Protein Modification, Bioconjugate Chem. 1995, vol. 6, pp. 62–69.

Ranganathan, D., et al., Synthesis of Totally Chiral, Multiple Armed, Poly Glu and Poly Asp Scaffoldings on Bifunctional Adamantane Core, Tetrahedron Letters, vol. 38, No. 7, pp. 1265–1268, 1997.

\* cited by examiner

A: R = -NH-carbamate(spacer)-AraC
B: R = -NH-amide(spacer)-AraC
C: R = -NH-urea(spacer)-AraC
D: R = -NH-thiocarbamate(spacer)-AraC
E: R = -NH-thioamide(spacer)-AraC
F: R = -NH-thiourea(spacer)-AraC
G: R = -NH-carbonate(spacer)-Camptothecin

POLYMER CONJUGATES OF BIOLOGICALLY ACTIVE AGENTS AND EXTENSION MOIETIES FOR FACILITATING CONJUGATION OF BIOLOGICALLY ACTIVE AGENTS TO POLYMERIC TERMINAL GROUPS

CROSS-REFERENCE TO RELATED APPLICATION

This application claims the benefit of priority from U.S. Patent Provisional Application Serial No. 60/193,726 filed Mar. 31, 2000, the contents of which are incorporated herein by reference.

TECHNICAL FIELD

The present invention relates to polymeric conjugates of biologically active agents and methods of preparing the same. In particular, the invention relates to the use of extension moieties, which increase the efficiency of the loading of active ingredients onto polymeric carriers.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols.

Prodrugs by definition are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs.

Incorporating a polymer as part of a prodrug system has been suggested to increase the circulating life of a drug. A brief overview of some previous work in the field is presented below.

Ohya, et al., J. *Bioactive and Compatible Polymers* Vol. 10 January, 1995, 51–66, discloses doxorubicin-PEG conjugates which are prepared by linking the two substituents via various linkages including esters. The molecular weight of the PEG used, however, is only about 5,000 at most. Thus, the in vivo benefits are not fully realized because the conjugates are substantially excreted prior to sufficient linkage hydrolysis.

Commonly-assigned PCT publication WO96/23794 describes bis-conjugates in which one equivalent of the hydroxyl-containing drug is attached to each terminal of the linear polymer. In spite of this advance, techniques which would further increase the payload of the polymer have been sought.

In another commonly-assigned PCT application, WO99/53951 (the '951 application), therapeutic polymeric conjugates with double or even greater therapeutic payloads are disclosed. Specifically, the polymers which are substantially linear, are designed to include multifunctional groups on both the alpha and omega terminus which are adapted for receiving up to four or more equivalents of a biologically active agent. Further work in this field has been done to address the problems which can occur when attempting to achieve complete or stochiometric loading of some active ingredients onto the multi-armed polymers. In particular situations, it has been found that it would be desirable to be able to provide more predictable and reproducible high degrees of loading. Such can be the case especially when steric hindrance or the molecular shape of the active ingredient reduces the likelihood of relatively complete loading of each multi-armed terminal group.

Commonly assigned U.S. Ser. No. 09/404,705 discloses still further bifunctional polymer conjugates. In particular, the application describes bifunctional polymers containing one equivalent of ara-C or a related anti-metabolite attached on each terminal. While reproducible and complete loading of such polymers is less of a concern than with the multi-armed terminal groups described above, improvements were nonetheless sought. The contents of each of the above-mentioned commonly-assigned patent applications and PCT international applications is incorporated herein by reference.

Thus, there continues to be a need to provide additional technologies for forming polymeric prodrugs of therapeutic moieties. The present invention addresses this need.

SUMMARY OF THE INVENTION

In one aspect of the invention, compounds of Formula (I) are provided:

wherein:

G is a linear or branched polymer residue;

$Y_1$ and $Y_2$ are independently O, S, or $NR_9$;

$M_1$–$M_3$ are independently O, S, or $NR_{10}$;

$M_4$ is X or Q;

wherein X is an electron withdrawing group and Q is a moiety containing a free electron pair positioned three to six atoms from $C(=Y_2)$;

B is a residue of an amine-containing moiety or a residue of a hydroxyl-containing moiety;

$R_{1-10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

a, b, c, d, e, f, g, h, i and n are each independently zero or a positive integer.

In preferred embodiments, G is a bifunctional polymer residue based on polyalkylene oxides such as poly(ethylene glycol) (PEG) and $M_1$–$M_3$ are O or $NR_{10}$ and $R_{10}$ is preferably H. $M_4$ is also preferably O or $NR_{10}$, where $R_{10}$ is preferably H.

In preferred aspects of this invention, the polymeric residue is substituted on both the proximal and the distal portion to provide the compounds of the formula:

$$B-\overset{Y_2}{\underset{\|}{C}}-[M_4]_i\text{-}\left[\overset{R_5}{\underset{R_6}{C}}\right]_h\left\{[M_3]_f\text{-}\left[\overset{R_3}{\underset{R_4}{C}}\right]_e\right\}_g[M_2]_d\text{-}\left[\overset{R_1}{\underset{R_2}{C}}\right]_c\left[\overset{Y_1}{\underset{\|}{C}}\right]_b[M_1]_a\text{-}(\overset{R_7}{\underset{R_8}{C}})_n\text{-}G\text{-} \quad (II)$$

$$-(\overset{R_7}{\underset{R_8}{C}})_n\text{-}[M_1]_a\text{-}\left[\overset{Y_1}{\underset{\|}{C}}\right]_b\left[\overset{R_1}{\underset{R_2}{C}}\right]_c[M_2]_d\left\{\left[\overset{R_3}{\underset{R_4}{C}}\right]_e[M_3]_f\right\}_g\left[\overset{R_5}{\underset{R_6}{C}}\right]_h[M_4]_i\text{-}\overset{Y_2}{\underset{\|}{C}}-B$$

where all variables are as previously defined.

When B is a residue of a hydroxyl-containing moiety or an amine-containing moiety, each B is attached via a preferably hydrolyzable linkage which attaches to the polymer residue terminus.

Examples of hydroxyl-containing moieties for which one or more of improved aqueous solubility, decreased antigenicity, prodrug and/or controlled release delivery is desired include chemotherapeutic compound residues such as anti-fungal compounds, including hydroxyl-containing triazoles, hydroxyl-containing echinocandins, hydroxyl-containing pneumocandins, etc, anti-cancer compounds such as camptothecin, paclitaxel, etoposide, anti-cancer platinum compounds containing OH groups, floxuridine or podophyllotoxin.

Examples of amine-containing moieties for which one or more of improved aqueous solubility, decreased antigenicity, prodrug and/or controlled release delivery is desired include antimetabolites such as Ara-C or gemcitabine. In still further embodiments, other oncolytic agents, non-oncolytic agents such as anti-inflammatory agents, including steroidal compounds, protease inhibitors such as AZT, as well as therapeutic low molecular weight peptides such as insulin are also contemplated.

For purposes of the present invention, the term "residue" shall be understood to mean that portion of a biologically active compound which remains after the biologically active compound has undergone a substitution reaction in which the prodrug carrier portion has been attached.

For purposes of the present invention, the term "alkyl" shall be understood to include straight, branched, substituted, e.g. halo-, alkoxy-, and nitro-$C_{1-12}$ alkyls, $C_{3-8}$ cycloalkyls or substituted cycloalkyls, etc. "Halo" shall be understood to include, for example, fluoro, chloro, bromo, iodo.

For purposes of the present invention, the term "substituted" shall be understood to include adding or replacing one or more atoms contained within a functional group or compound with one or more different atoms.

The term "sufficient amounts" for purposes of the present invention shall mean an amount which achieves a therapeutic effect as such effect is understood by those of ordinary skill in the art.

One of the chief advantages of the compounds of the present invention is that the prodrugs have a more predictable degree of loading which is achieved by using the extender (or spacer) moieties described herein between the polymer residue ends and the parent therapeutic molecules. The substantially uniform polymeric conjugates are thus easy to analyze and are highly reproducible. The rate of hydrolysis is also predictable and reproducible from batch to batch. Still, a further advantage is that in certain preferred embodiments, in which the polymer portion has a molecular weight of from about 20 to about 50 kDa, conjugates containing anti-tumor agents are believed to passively target tumors and thus enhance the effectiveness of the anti-tumor parent compound on solid tumors. While applicants are not bound by theory, it is believed that tumor proteases, alone and/or in combination with peptidases, cleave the covalent linkage between the polymer and active agent, thus freeing the parent active agent within the tumor.

Methods of making and using the compounds and conjugates described herein are also provided.

DETAILED DESCRIPTION OF THE INVENTION

A. Formula (I) and (II)

Figure 1:
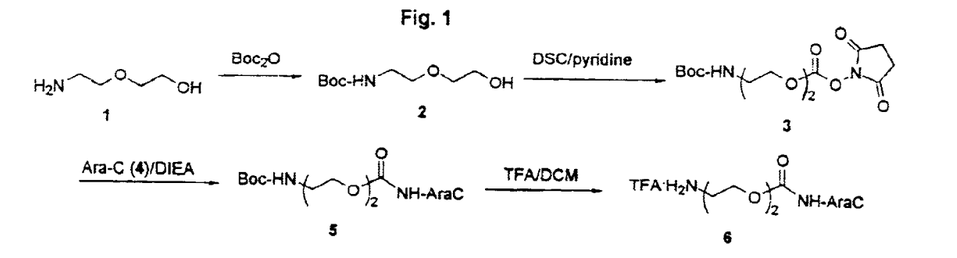
FIGS. 1–8 schematically illustrate the synthesis of compounds described in the specification.
Figure 2:
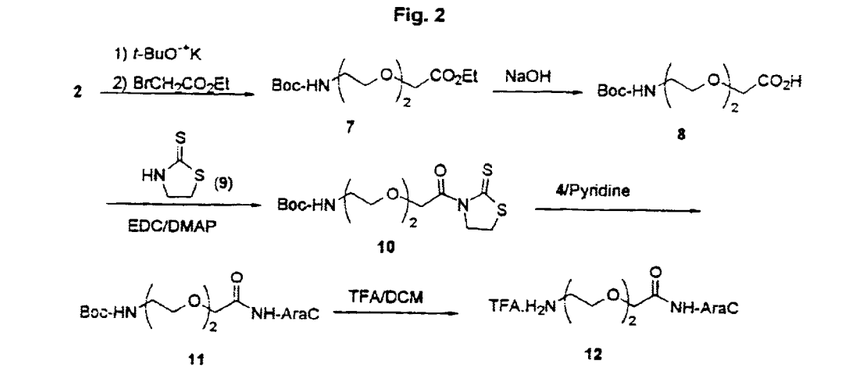
Figure 3:
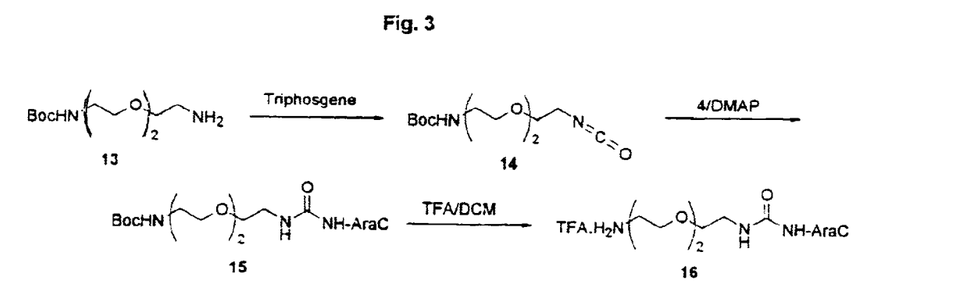
Figure 4:
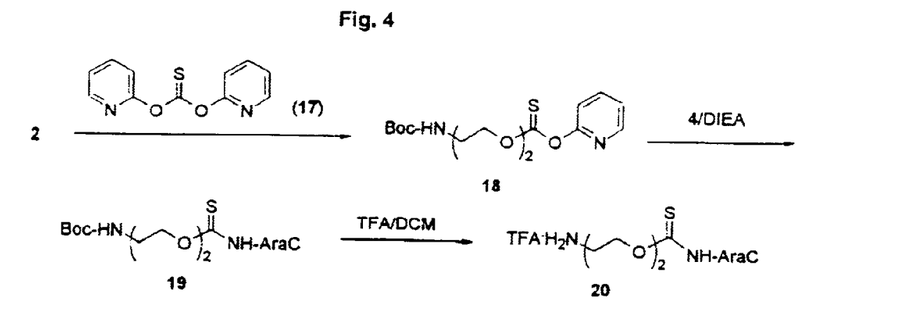
Figure 5:
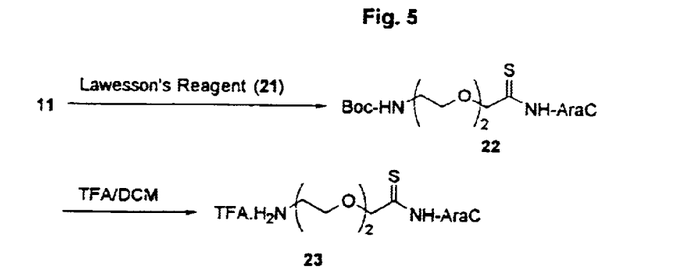
Figure 6:
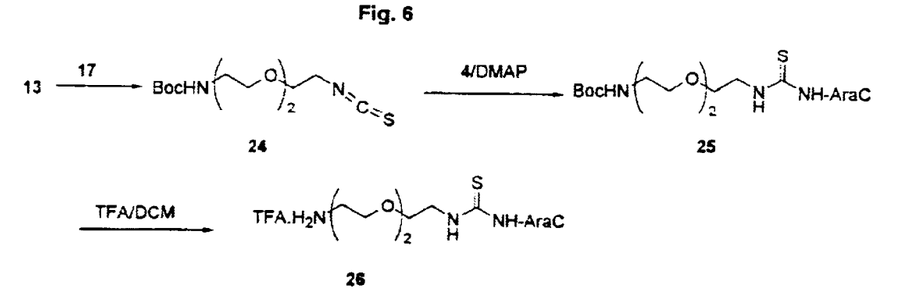
Figure 7:
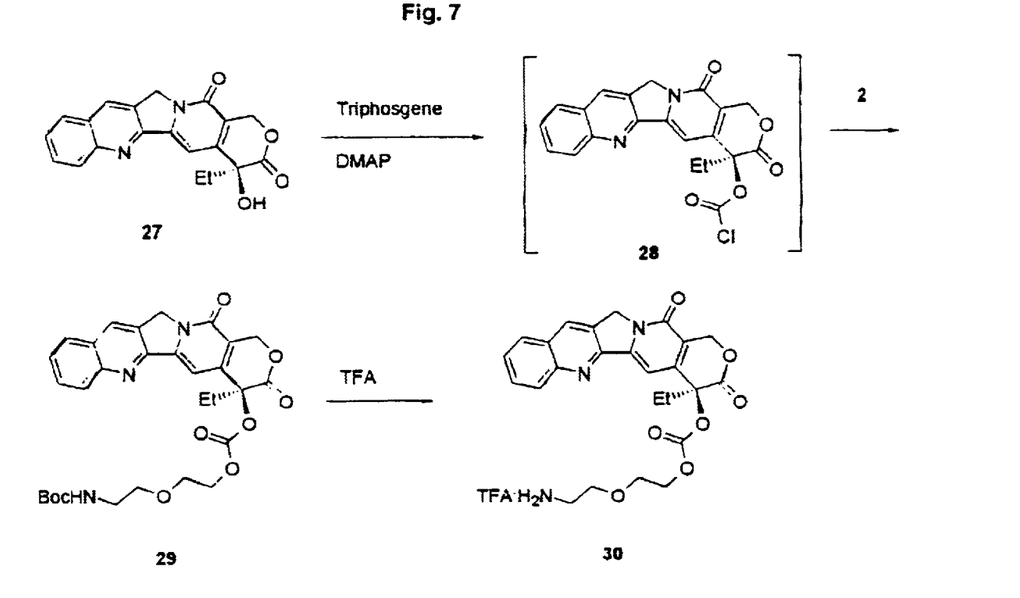
Figure 8:
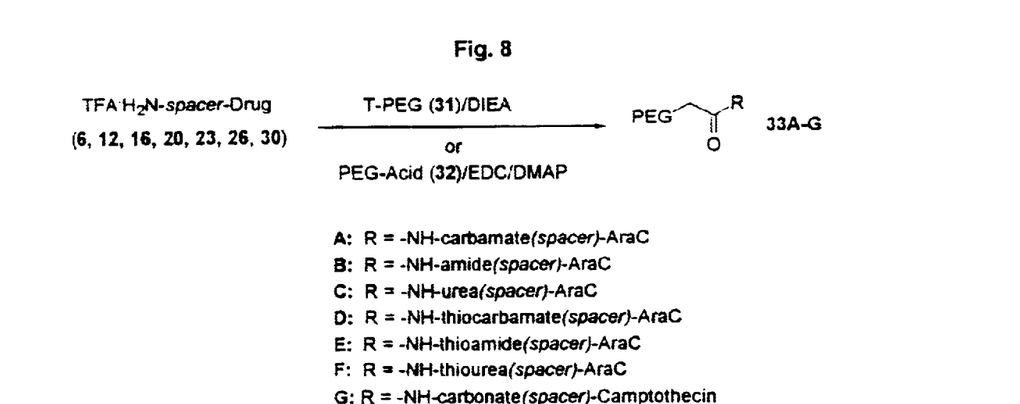

Preferred polymeric conjugates are of the formulae:

$$G-(\overset{R_7}{\underset{R_8}{C}})_n\text{-}[M_1]_a\text{-}\left[\overset{Y_1}{\underset{\|}{C}}\right]_b\left[\overset{R_1}{\underset{R_2}{C}}\right]_c[M_2]_d\left\{\left[\overset{R_3}{\underset{R_4}{C}}\right]_e[M_3]_f\right\}_g\left[\overset{R_5}{\underset{R_6}{C}}\right]_h[M_4]_i\text{-}\overset{Y_2}{\underset{\|}{C}}-B \quad (I)$$

or $$B-\overset{Y_2}{\underset{\|}{C}}-[M_4]_i\text{-}\left[\overset{R_5}{\underset{R_6}{C}}\right]_h\left\{[M_3]_f\text{-}\left[\overset{R_3}{\underset{R_4}{C}}\right]_e\right\}_g[M_2]_d\text{-}\left[\overset{R_1}{\underset{R_2}{C}}\right]_c\left[\overset{Y_1}{\underset{\|}{C}}\right]_b[M_1]_a\text{-}(\overset{R_7}{\underset{R_8}{C}})_n\text{-}G\text{-} \quad (II)$$

$$-(\overset{R_7}{\underset{R_8}{C}})_n\text{-}[M_1]_a\text{-}\left[\overset{Y_1}{\underset{\|}{C}}\right]_b\left[\overset{R_1}{\underset{R_2}{C}}\right]_c[M_2]_d\left\{\left[\overset{R_3}{\underset{R_4}{C}}\right]_e[M_3]_f\right\}_g\left[\overset{R_5}{\underset{R_6}{C}}\right]_h[M_4]_i\text{-}\overset{Y_2}{\underset{\|}{C}}-B$$

wherein: G is a linear or branched polymer residue;

$Y_1$ and $Y_2$ are independently O, S, or $NR_9$;

$M_1$–$M_3$ are independently O, S, or $NR_{10}$;

$M_4$ is X or Q;

wherein X is an electron withdrawing group such as O, S, SO, $SO_2$, or $NR_{11}$ where $R_{11}$ is H, $C_{1-6}$ alkyl, any of the other groups which comprise $R_{10}$ and Q is a moiety containing a free electron pair positioned three to six atoms from $C(=Y_2)$;

B is a residue of an amine-containing moiety or a residue of a hydroxyl-containing moiety;

$R_{1-10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

a, b, c, d, e, f, g, h, i and n are each independently zero or a positive integer, preferably zero, one or two.

B. Substantially Non-Antigenic Polymers

Within formulae (I) and (II), G is a polymer residue which is preferably substantially non-antigenic. In preferred aspects of the invention, the polymer residue is based on polyalkylene oxides such as poly(ethylene glycol) (PEG). The general formula for PEG and its derivatives is where (x) represents the degree of polymerization (i.e. from about 10 to about 2,300) or number of repeating units in the polymer chain and is dependent on the molecular weight of the polymer, (A) is H or a capping group such as aminoalkyl, carboxyalkyl, haloalkyl, or other activating group and (A') is the same as (A) or another (A) moiety. In alternative aspects, the polymer residue is a poly(propylene glycol) (PPG). Thus, the G moiety residues are preferably $O-(CH_2CH_2O)_x$ or $O-(CH(CH_3)CH_2O)_x$, wherein x is the degree of polymerization.

Also useful are branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference.

As an alternative to the preferred PAO-based polymers, other effectively non-antigenic, terminally functionalized polymers can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be understood by those of ordinary skill that the water-soluble polymer, e.g. PEG, can be terminally functionalized using standard organic synthesis techniques which are reported in the literature to add the desired leaving group for facilitating attachment of the polymer to the target or parent compound via reacting with an available amino or hydroxyl group. Alternatively, functionalized PEG's are available from commercial suppliers such as Aldrich Chemical Company of Milwaukee, Wis. Thus, the PEG can be terminally modified to include moieties of group A which include hydrogen, $CO_2H$, $C_{1-6}$ alkyl moieties and (II')

wherein all of the variables are as set forth above.

In order to provide the desired linkage, activated polymers such as PEG diacids can be used as well as PEG diamines and PEG diols. Suitable PAO acids can be synthesized by first converting PEG-OH to an ethyl ester followed by saponification. See also Gehrhardt, H., et al. *Polymer Bulletin* 18:487 (1987) and Veronese, F. M., et al., *J. Controlled Release* 10; 145 (1989). Alternatively, the PAO-acid can be synthesized by converting PEG-OH into a t-butyl ester followed by acid cleavage. See, for example, commonly assigned U.S. Pat. No. 5,605,976. The disclosures of each of the foregoing are incorporated by reference herein. Although PAO's and PEG's can vary substantially in number average molecular weight, polymers ranging from about 2,000 to about 100,000 are usually selected for the purposes of the present invention. Molecular weights of from about 5,000 to about 80,000 are preferred and 20,000 to about 50,000 are particularly preferred. The weight average molecular weight (Mw) of the polymer selected for inclusion in the prodrug must be sufficient so as to provide sufficient circulation of the prodrug before hydrolysis of the linker. Preferably, G is $O-(CH_2CH_2O)_x$ and x is a positive integer selected so that the Mw is at least about 20,000.

C. The Linkage Moieties

1. The M Groups

Within the Formulae (I) and (II), $M_{1-3}$ are preferably independently selected from O, S, $NR_{10}$ where $R_{10}$ is preferably H or a lower (i.e. $C_{1-4}$) alkyl. $M_4$, on the other hand, is either X or Q which are defined above. $M_4$ is preferably X, and X preferably either O or $NR_{10}$. $R_{10}$ is also preferably H.

2. Q Portion of the Linker

In alternative aspects, $M_4$ can be Q which represents a moiety containing a free electron pair positioned three to six atoms, and preferably five atoms, from the $C(=Y_2)$ moieties. Q can be selected from the non-limiting list of cycloalkyls, alyls, aralkyl groups substituted with O, S or $NR_{11}$, where $R_{11}$ is defined as the same group as that listed above with regard to $R_{1-10}$. Preferably, $R_{11}$ is H, a $C_{1-6}$ alkyl or substituted $C_{1-6}$ alkyl. The free electron pair can be anywhere along the Q moiety as long as the defined spacing between the free electron pair and the $C(=Y_2)$ is maintained. Thus, Q assists hydrolysis of the prodrug linkage by anchimeric assistance because the free electron pair can generate a three- to six-membered, but preferably five-membered, ring intermediate upon hydrolysis preferably of the ester linkage.

D. Synthesis of Polymeric Prodrug Transport System

The prodrugs of the present invention can be prepared using standard organic synthesis techniques. If necessary, the spacer is attached to the polymer and activated by attaching a terminal leaving group. The activated polymer portion can be obtained from either commercial sources or synthesized by the artisan without undue experimentation. For example, PEG-diacids are available from commercial suppliers such as Aldrich Chemical Company of Milwaukee, Wis. or they can be synthesized as described in commonly assigned U.S. Pat. No. 5,605,976, the contents of which are incorporated herein by reference. When amide linkages are sought, an activated PEG such as a bis-thiazolidine-2-thione-activated PEG (T-PEG) such as that described in commonly assigned U.S. Pat. No. 5,349,001 can be used. Alternatively, when a carbamate linkage is sought, a suitably activated PEG such as PEG-di-chloroformate or bis-SC-PEG, prepared as described in commonly assigned U.S. Pat. No. 5,122,614, or a bis-p-nitrophenyl chloroformate-activated PEG can be used. The disclosure of each of the two mentioned U.S. patents are incorporated herein by reference. The urea-linked transport systems can be prepared using bis-PEG-isocyanate generated by reacting bis-PEG-$NH_2$ with phosgene or triphosgene and a tertiary base such as diisopropylethylamine (DIEA). Regardless of the source, the activated polymer is then reacted with the amine-containing or hydroxyl-containing target to form the conjugate. It will also be understood that the corresponding thio derivatives can be made in similar fashions by using the corresponding thio-containing PEG derivatives, e.g. bis-PEG-isothiocyante, etc. See also the Examples below.

For purposes of illustration, the methods of synthesis for the present invention include a) reacting a biologically active moiety having an unprotected amine or hydroxyl group with a compound of the formula (III)

wherein $B_1$ is OH, a leaving group capable of reacting with an unprotected amine or unprotected hydroxyl group;

$B_2$ is a cleavable protecting group;

$Y_2$ is O, S, or $NR_9$;

$M_2$–$M_3$ are independently O, S, or $NR_{10}$, $M_4$ is X or Q;

wherein X is an electron withdrawing group and Q is a moiety containing a free electron pair positioned three to six atoms from $C(=Y_2)$;

$R_{3-6}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

d, e, f, g, h, and i are each independently zero or a positive integer; to form a protected intermediate of the formula:

(IV)

wherein

B is a residue of an amine-containing moiety or a residue of a hydroxyl-containing moiety;

b) deprotecting the resultant intermediate by removing $B_2$; and c) reacting the deprotected intermediate with a compound of the formula (V)

wherein $B_3$ is a leaving group;

G is a linear or branched polymer residue;

$Y_1$ is O, S, or $NR_9$;

$M_1$ is O, S, or $NR_{10}$;

$R_1$, $R_2$, $R_7$ and $R_8$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; and a, b and c are each independently zero or a positive integer, whereby a polymeric conjugate is formed.

See also the Figures and the Examples for additional details concerning the reactions related hereto.

Attachment of the B moiety, i.e. containing the unprotected amine or unprotected hydroxyl, can also be carried out in the presence of a coupling agent. A non-limiting list of suitable coupling agents includes 1,3-diisopropylcarbodiimide (DIPC), any suitable dialkyl carbodiimides, 2-halo-1-alkyl-pyridinium halides, (Mukaiyama reagents), 1-(3-dimethylamino-propyl)-3-ethyl carbodiimide (EDC), 1-propanephosphonic acid cyclic anhydride (PPACA) and phenyl dichloro-phosphates, etc. which are available, for example, from commercial sources such as Sigma-Aldrich Chemical, or synthesized using known techniques. Preferably EDC is used in pyridine to couple the ara-C derivative (IV) with PEG-carboxylic acid (V). Alternatively, a PEG-carboxylic activated imide, T-PEG derivative, is reacted with ara-C or ara-C derivative in pyridine to produce the desired conjugate (prodrug). Other inert solvents such as methylene chloride, chloroform, toluene, DMF or mixtures thereof can also be used. The reaction is also preferably conducted at a temperature from 20° C. up to about 45° C., in the presence of a base, such as 4-(dimethylamino)-pyridine, diisopropyl-ethylamine, pyridine, triethylamine, etc. to neutralize any acids generated.

In an alternative method of synthesis, the polymeric transport system and extender or spacer are synthetically combined using standard coupling techniques and the therapeutic or parent compound is attached thereafter. In such situations, the following reaction scheme is followed:

a) reacting a polymer-spacer intermediate of the formula.

(V)

wherein all other variables are the same as set forth above in the description of the first method and thereafter reacting intermediate with a biologically active moiety having an unprotected amine or hydroxyl group to form the polymeric conjugate.

The artisan of ordinary skill will realize that the dimer or disubstituted polymeric conjugates are made in the same way as that illustrated above using bifunctional PEG derivatives in place of the mono-PEG shown. Regardless of the synthesis selected, some of the preferred compounds which result from the synthesis techniques described herein include:

-continued

The corresponding dimer or bifunctional derivatives are of the formulae:

In especially preferred embodiments, B is ara-C or a derivative thereof corresponding to the formula:

wherein $R_{12-13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls, substituted $C_{1-6}$ heteroalkyls;

$R_{14-18}$ are independently selected from alkoxy, e.g. $OR_{19}$ or, in the alternative, H, OH, $N_3$, $NHR_{20}$, $NO_2$ or CN, fluoro, chloro, bromo, iodo, where $R_{19-20}$ are independently selected from the same group which defines $R_{12-13}$ and is preferably H or a $C_{1-4}$ alkyl.

Residues of Amine-containing Compounds

In addition to the ara-C compounds described above, B can also be a residue of other amine-containing compounds, a non-limiting list of such suitable compounds include residues of organic compounds, enzymes, proteins, polypeptides, etc. anti-anxiety agents, gastrointestinal agents, central nervous system-activating agents, analgesics, fertility agents, contraceptive agents, anti-inflammatory agents, steroidal agents, anti-urecemic agents, vasodilating agents, vasoconstricting agents, etc.

Suitable proteins, polypeptides, enzymes, peptides and the like having at least one available amino group for polymer attachment include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. either after attachment to the polymeric transport or, if relevant, after the parent compound has been hydrolyzed and released.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a biological polymer demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

Preferably, when it is desired that the amino-containing B moiety be released as part of a polymeric prodrug, it is desirable that the amine residue which is attached to the polymer also be in proximity to a highly electron-withdrawing moiety such as a pyramidimyl or purinyl or other heterocyclical aromatic or aromatic containing group containing an electron-withdrawing group such as $NO_2$, CF, etc. so that prodrug system releases and regenerates the parent compound.

Residues of Hydroxyl Containing Compounds a. Camptothecin and Related Topoisomerase I Inhibitors

Camptothecin is a water-insoluble cytotoxic alkaloid produced by *Camptotheca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for attachment to the polymeric systems of the present invention. Camptothecin and certain related analogues share the structure:

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e.—O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

For purposes of the present invention, the term "taxane" includes all compounds within the taxane family of terpenes. Thus, paclitaxel, 3'-substituted tert-butoxy-carbonyl-amine derivatives (e.g. Taxotere™) and the like as well as other analogs which are readily synthesized using standard organic techniques or are available from commercial sources such as Sigma Chemical of St. Louis, Mo. are within the scope of the present invention. Representative taxanes are shown below.

Paclitaxel: R'$_1$=C$_6$H$_5$; R'$_2$=CH$_3$CO; Taxotere: R'$_1$=(CH$_3$)$_3$CO; R'$_2$=H

These derivatives have been found to be effective anticancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. The only limitation on the taxane is that it must be capable of undergoing a hydroxyl based substitution reaction such as at the 2' position. Pactitaxel, however, is a preferred taxane.

c. Additional Biologically-Active OH-Containing Moieties

In addition to the foregoing molecules, the prodrugs of the present invention can be prepared using many other compounds. For example, biologically-active compounds such as podophyllotoxin:

or triazole-based antifungal agents such as fluconazole:

or ciclopirox:

can be used.

The parent compounds selected for prodrug forms need not be substantially water-insoluble, although the polymer-based prodrugs of the present invention are especially well suited for delivering such water-insoluble compounds.

It is noted that parent compounds suitable for incorporation into the polymeric prodrug compositions of the invention, may themselves be substances/compounds which are not active after hydrolytic release from the linked composition, but which will become active after undergoing a further chemical process/reaction. For example, an anticancer drug that is delivered to the bloodstream by the polymeric transport system, may remain inactive until entering a cancer or tumor cell, whereupon it is activated by the cancer or tumor cell chemistry, e.g., by an enzymatic reaction unique to that cell.

After conjugation, the remaining portion of the amine-containing or hydroxyl-containing compound is referred to as the residue of the unconjugated compound.

E. Method of Treatment

Another aspect of the present invention provides methods of treatment for various medical conditions in mammals. The methods include administering to the mammal in need of such treatment, an effective amount of a polymer conjugate, such as an ara-C-PEG conjugate, which has been prepared as described herein. The compositions are useful for, among other things, treating neoplastic disease including leukemias, reducing tumor burden, preventing metastis of neoplasms and preventing recurrences of tumor/neoplastic growths in mammals.

The amount of the polymer conjugate administered will depend upon the specific ara-C molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug ara-C is administered in amounts ranging from about 5 to about 5,000 mg/m$^2$ per day, based on the amount of the ara-C moiety. Gemcitabine polymer conjugates prodrugs are also administered in amounts ranging from about 5 to about 2,000 mg/m$^2$ per day. The range set forth above is illustrative and those skilled in the art will determine the optimal dosing of the selected prodrug based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may be also be by infusion into a body space or cavity, as well as by inhalation and/or intranasal routes. In preferred aspects of the invention, however, the prodrugs are parenterally administered to mammals in need thereof.

F. EXAMPLES

The following examples serve to provide further appreciation of the invention but are not meant in any way to restrict the effective scope of the invention. The underlined and bold-faced numbers recited in the Examples correspond to those shown in the Figures.

General. All reactions were run under an atmosphere of dry nitrogen or argon. Commercial reagents were used without further purification. All PEG compounds were dried under vacuum or by azeotropic distillation (toluene) prior to use. $^1$H spectra were obtained with a JEOL FT NMR System JNM GSX-270 or Varian Mercury VX-300 instrument using deuteriochloroform as solvent unless specified. $^{13}$C NMR spectra were obtained at 67.80 MHz on the JNM GSX-270 or 75.46 MHz on the Varian Mercury VX-300. Chemical shifts (δ) are reported in parts per million (ppm) downfield from tetramethylsilane (TMS) and coupling constants (J values) are given in hertz (Hz). All PEG conjugated compounds were dissolved (~15 mg/mL) in sterile saline (0.9%) for injection prior to in vivo drug treatments and were given as their ara-C equivalents (absolute amount of ara-C given).

HPLC Method. Analytical HPLC's were performed using a C8 reversed phase column (Beckman, ultrasphere) under isocratic conditions with an 80:20 mixture (v/v) of methanol-water as mobile phase. Peak elutions were monitored at 254 nm using a UV detector. To detect the presence of any free PEG and also to confirm the presence of pegylated product, an evaporative light scattering detector (ELSD), Model PL-EMD 950 (Polymer Laboratories), was employed. Based on ELSD and UV analysis, all the final pegylated products were free of native drug and were ≧95% pure by HPLC.

Analysis of Ara-C Content in PEG Derivatives. For the determination of the ara-C content in PEG derivatives, $N^4$-acetylcytidine was used as the basis because of the absorbance change due to the acylation of ara-C. The UV absorbance of $N^4$-acetylcytidine in $H_2O$ was determined at 257 nm for six different concentrations ranging from 0.01 µmol/mL to 0.05 µmol/mL. From the standard plot of absorbance vs. concentration, the absorption coefficient, ε, of $N^4$-acetylcytidine was calculated to be 36.4 (O.D. at 257 nm for 1 mg/mL with 1.0 cm light path). Pegylated ara-C derivatives were dissolved in $H_2O$ at an approximate concentration of 0.015 µmol/mL (based on a MW of 40 kDa) and the UV absorbance of these compounds at 257 nm was determined. Using this value and employing the absorption coefficient, ε, obtained from the above, the concentration of ara-C in the sample was determined. Dividing this value by the sample concentration provided the percentage of ara-C in the sample. See also, Greenwald, R. B., et al., "Drug Delivery Systems: Water Soluble Taxol 2-Poly(ethylene glycol) Ester Prodrugs-Design and In Vivo Effectiveness." *J. Med. Chem.* 1996, 39, 424–431, the contents of which are incorporated herein by reference.

Determination of Rates of Hydrolysis of PEG Prodrugs. The rates of hydrolysis were obtained by employing a C8 reversed phase column (Zorbax SB-C8) using a gradient mobile phase consisting of (a) 0.1 M triethylammonium acetate buffer and (b) acetonitrile. A flow rate of 1 mL/minute was used, and chromatograms were monitored using a UV detector at 254 nm for daunorubicin and 280 nm for ara-C. For hydrolysis in buffer, PEG derivatives were dissolved in 0.1 M pH 7.4 PBS at a concentration of 5 mg/mL, while for hydrolysis in plasma, the derivatives were dissolved in distilled water at a concentration of 20 mg/100 µL and 900 µL of rat plasma was added to this solution. The mixture was vortexed for 2 minutes and divided into 2 mL glass vials with 100 µL of the aliquot per each vial. The solutions were incubated at 37° C. for various periods of time. A mixture of methanol-acetonitrile (1:1, v/v, 400 µL) was added to a vial at the proper interval and the mixture was vortexed for 1 minute, followed by filtration through 0.45 mm filter membrane (optionally followed by a second filtration through 0.2 mm filter membrane). An aliquot of 20 µL of the filtrate was injected into the HPLC. On the basis of the peak area, the amounts of native compound and PEG derivative were estimated, and the half-life of each compound in different media was calculated using linear regression analysis from the disappearance of PEG derivative.

Abbreviations. DCM (dichloromethane), DIEA (N,N-diisopropylethylamine), DMAP (4-(dimethylamino) pyridine), DSC (N,N-disuccinimidyl carbonate), EDC (1-ethyl-3-(3-dimethylaminopropyl)carbodiimide), HOBT (1-hydroxybenzotriazole), IPA (2-propanol), NMM (N-methylmorpholine), TFA (trifluoroacetic acid).

Example 1

2-(2-Boc-aminoethoxy)-ethanol (2). This compound was prepared by a modification of the procedure described by, Lebeau, L, et al., "Synthesis of New Phospholipids Linked to Steroid-Hormone Derivatives Designed for Two-Dimensional Crystallization of Proteins," Helv. Chim Acta 1991, 74, 1697–1706, the contents of which are incorporated herein by reference. A solution of di-tert-butylcarbonate (10.27 g, 47.2 mmol) in chloroform (40 mL) was added to a solution of 2-(2-amninoethoxy)-ethanol (1, 5.0 g, 47.62 mmol) in chloroform (40 mL) and the mixture was stirred at room temperature for 1.5 hours. The solution was washed with water (30 mL) and the organic layer was dried over anhydrous $MgSO_4$ and concentrated in vacuo to give the product (9.6 g, 99%): $^1$H NMR δ 1.45 (s, 9H, t-Bu), 3.32 (m, 2H, $NHCH_2$), 3.43 (bs, 1H, OH), 3.56 (m, 4H, $CH_2OCH_2$), 3.73 (t, 2H, J=5.4, $CH_2OH$), 5.43 (bs, 1H, NH); $^{13}$C NMR δ 28.21, 40.21, 61.31, 70.08, 72.14, 77.18, 79.06, 156.06.

Example 2

2-(2-Boc-aminoethoxy)-ethanol NHS carbonate (3). A mixture of 2 (1.0 g, 4.88 mmol), DSC (1.5 g, 5.86 mmol), and anhydrous pyridine (474 mg, 6.0 mmol) in anhydrous chloroform (25 mL) was stirred at 25–30° C. overnight. The reaction mixture was washed with 0.5N HCl then dried over anhyd $MgSO_4$. Evaporation of the solvent gave the product (1.5 g, 96%): $^1$H NMR δ 1.45 (s, 9H, t-Bu), 2.84 (bs, 4H, NHS), 3.32 (m, 2H, $NHCH_2$), 3.56 (t, 2H, J=4.9, $CH_2O$), 3.74 (t, 2H, J=4.3, $OCH_2$), 4.47 (t, 2H, J=4.3, $CH_2OC(=O)$ ONHS), 5.01 (br s, 1H, NH); $^{13}$C NMR δ 25.00, 27.92, 39.81, 67.57, 69.59, 69.89, 77.20, 78.56, 151.18, 155.58, 168.60.

Example 3

2-(2-Boc-aminoethoxy)-ethanol Ara-C carbamate (5). A mixture of 3 (1.0 g, 3.13 mmol), ara-C (4, 760 mg, 3.13 mmol), and DIEA (605 mg, 4.69 mmol) in anhydrous DMF (50 mL) and anhydrous pyridine (20 mL) was stirred at 35–40° C. overnight. The reaction mixture was concentrated and the residue purified by silica gel column chromatography (100% ethyl ether→20% MeOH in $CHCl_3$) to give 201.8 mg (14%) of product: $^{13}C$ NMR δ 25.34, 28.26, 40.10, 61.52, 64.85, 68.44, 70.02, 75.06, 79.28, 85.17, 92.40, 146.41, 152.74, 155.69, 156.27, 162.63, 173.82.

Example 4

2-(2-Aminoethoxy)-ethanol Ara-C carbamate TFA salt (6). Compound 4 (210 mg, 0.44 mmol) was dissolved in TFA (2 mL) and DCM (4 mL) and the solution was stirred at room temperature for 1.5 hours. The solvent was removed in vacuo and the residue crystallized from DCM-ether to give 200 mg (93%) of product: $^{13}C$ NMR ($CD_3OD+CDCl_3$) δ 24.61, 38.85, 60.52, 62.23, 66.03, 68.12, 74.59, 76.01, 85.39, 87.56, 94.10, 115.72 (q), 146.84, 152.28, 153.78, 160.33, 160.62 (q), 160.91, 161.60, 173.05.

Example 5

2-(2-Boc-aminoethoxy)-ethoxy]-acetic acid ethyl ester (7). To a solution of 2 (4.5 g, 24.39 mmol) in toluene (100 mL) was added 1.0M potassium t-butoxide in t-butanol (36.6 μL, 36.6 mmol) at –10 to –20° C. for 1.5 hours and followed by addition of ethyl bromoacetate (8.146 g, 48.78 mmol). The resulting mixture was stirred for 3 hours at 10 to 20° C., followed by the addition of 0.25 N HCl (50 mL). The organic layer was separated and dried over anhydrous $MgSO_4$. The solvent was removed and the residue purified with silica gel column chromatography (30 to 50% ethylacetate in hexane) to give 4.0 g (63%) of product: $^1H$ NMR δ 1.29 (t, 3H, J=7.29, $CH_2CH_3$), 1.44 (s, 9H, Boc), 3.31 (m, 2H, $CH_2CH_2$), 3.55 (m, 2H, $CH_2CH_2$), 3.66–3.75 (m, 4H, $CH_2CH_2$), 4.14 (s, 2H, $CH_2C$(=O)O), 4.22 (q, 2H, J=7.29, $CH_2CH_3$), 5.20 (br s, 1H, NH); $^{13}C$ NMR δ 13.85, 28.06, 40.04, 60.44, 68.29, 69.94, 70.52, 78.68, 155.72, 170.02. Anal. ($C_{13}H_{25}NO_6 \cdot 1/4 H_2O$) C, H, N.

Example 6

[2-(2-Boc-aminoethoxy)-ethoxy]-acetic acid (8). A solution of NaOH (5.0 g, 0.125 mol) in $H_2O$ (5 mL) and ethanol (50 mL, added after NaOH is dissolved in water) was added slowly to a solution of 7 (4.0 g, 0.014 mol) in ethanol (40 mL) in an ice bath and the temperature was kept <20° C. during the addition. After the addition the mixture was stirred for 2 hours, followed by acidification with 6N HCl to adjust pH to 2.5 with cooling. The mixture was filtered and the filter cake was washed with ethanol. The filtrate was concentrated in vacuo and the residue was partitioned between $DCM/H_2O$ to give the product (2.55 g, 75%): $^1H$ NMR δ 1.45 (s, 9H, Boc), 3.31 (n, 2H, $CH_2CH_2$), 3.55 (m, 2H, $CH_2CH_2$), 3.66–3.75 (m, 4H, $CH_2CH_2$), 4.20 (s, 2H, $CH_2C$(=O)O), 5.20 & 6.25 (br s, 1H, NH), 5.31 (s, 1H, COOH); $^{13}C$ NMR δ 28.21, 40.15, 53.32, 68.20, 70.12, 70.77, 79.55, 80.05, 156.12, 173.38.

Example 7

(2-{2-[2-Oxo-2-(2-thioxo-thiazolidin-3-yl)-ethoxy]-ethoxy}-ethyl)carbamic acid tert-butyl ester (10). A mixture of 8 (2.5 g, 9.506 mmol), 2-mercaptothiazoline (9, 2.262 g, 19.012 mmol), EDC-HCl (3.65 g, 19.012 mmol), and DMAP (4.639 g, 38.024 mmol) in DCM (150 mL) was stirred at 0° C. to room temperature overnight. The solution was diluted with DCM (100 mL) and washed with 1% $NaHCO_3$ (100 mL) followed by 0.5N HCl (100 mL×2). The organic layer was dried over anhyd $MgSO_4$ and the solvent was removed to give the crude product which has 2-mercaptothiazoline: $^{13}C$ NMR δ 27.74, 28.06, 29.24, 40.02, 53.32, 55.23, 69.80, 69.97, 70.45, 73.17, 79.05, 155.70, 171.52, 200.96.

Example 8

$N^4$-[2-(2-Boc-aminoethoxy)-ethoxy]-acetic acid amide ara-C (11). A mixture of 10 (748.3 mg, 2.06 mmol) and 4 (1.5 g, 6.17 mmol) in anhydrous pyridine (60 mL) was stirred at 30–35° C. overnight. The solvent was removed and the residue was dissolved in minimum amount of DMF to be purified by silica gel column chromatography to give product (250 mg, 25%): $^{13}C$ NMR δ 28.23, 39.98, 61.41, 68.05, 69.56, 70.08, 70.25, 71.03, 75.01, 77.20, 79.06, 85.25, 87.88, 96.05, 146.96, 155.73, 156.31, 161.46, 170.78.

Example 9

$N^4$-[2-(2-aminoethoxy)-ethoxy]-acetic acid amide ara-C TFA salt (12). Prepared from 11 in 99% yield as described for the preparation of 6: $^{13}C$ NMR ($CDCl_3+CD_3OD$) δ 38.63, 60.05, 66.45, 69.19, 69.39, 70.55, 74.56, 85.45, 87.62, 95.05, 115.72 (q), 146.96, 155.47, 160.91, 170.86.

Example 10

Urea derivative of ara-C: Compound (15). Triphosgene (308.2 mg, 1.04 mmol) and pyridine (307.1 mg, 3.88 mmol) are added to a solution of 2-amino-2'-Boc-aminoethylene glycol diethyl ether using a procedure similar to that described by Zuckermann, R. N., et al., "Discovery of Nanomolar Ligands For 7-Transmembrane G-Protein-Coupled Receptors From A Diverse N-(Substituted) Glycine Peptoid Library," *J. Med. Chem.* 1994, 37, 2678–2685, the contents of which are incorporated herein by reference. (13, 384.4 mg, 1.55 mmol) in chloroform (30 mL) and the mixture is stirred at 35–40° C. for 3 h followed by cooling to room temperature. Compound 4 (942.8 mg, 3.88 mmol) and DMAP (474 mg, 3.88 mmol) are added to the solution of isocyanate, 14, and the mixture is stirred at 35–40° C. overnight. The reaction solution is washed with 0.5 N HCl (3×10 mL), water (10 mL) and dried over anhyd $MgSO_4$, followed by removal of the solvent in vacuo. The residue is purified by silica gel column chromatography (0→20% MeOH in $CHCl_3$) to give product.

Example 11

TFA salt of Ura derivative: Compound (16). Compound 15 is subjected to the conditions as described for the preparation of 6 to give 16.

Example 12

2-(2-Boc-aminoethoxy)-ethanol 2-pyridyl thiocarbonate (18). A mixture of 2 (1.0 g, 4.88 mmol), di-2-pyridyl thionocarbonate prepared as described by Kim, S., et al., "Di-2-pyridyl Thionocarbonate. A New Reagent For The Preparation Of Isothiocyanates And Carbodiimides," *Tet. Lett.* 1985, 26, 1661–1664, the contents of which are incorporated herein by reference, (17, 1.36 g, 5.86 mmol), and anhydrous pyridine (474 mg, 6.0 mmol) in anhydrous chloroform (25 mL) is stirred for 3 hours at room temperature. The reaction mixture is washed with 0.5N HCl then dried over anhydrous $MgSO_4$, followed by evaporation of the solvent to give the product.

Example 13

2-(2-Boc-aminoethoxy)-ethanol 2-pyridyl thiocarbamate ara-C (19). Compound 18 is subjected to the conditions as described for the preparation of 5 to give 19.

Example 14

2-(2-Aminoethoxy)-ethanol 2-pyridyl thiocarbamate ara-C TFA salt (20). Compound 19 is subjected to the conditions as described for the preparation of 6 to give 20.

Example 15

$N^4$-[2-(2-Boc-aminoethoxy)-ethoxy]-acetic acid thioamide ara-C (22). A mixture of 11 (0.5 g, 1.024 mmol) and Lawesson's reagent, see Cava, M. P., et al, "Thionation Reactions of Lawesson's Reagents," *Tetrahedron* 1985, 41, 5061–5087, the contents of which are incorporated herein by reference, (248.4 mg, 0.61 mmol) in THF (10 mL) is refluxed for 5 hours and the solvent is removed in vacuo. The residue is purified by silica gel column chromatography (0→20% MeOH in $CHCl_3$) to give product.

Example 16

$N^4$-[2-(2-Aminoethoxy)-ethoxy]-acetic acid thioamide ara-C TFA salt (23). Compound 22 is subjected to the conditions as described for the preparation of 6 to give 23.

Example 17

Thiourea derivative of ara-C: Compound (25).

Compound 17 (241.6 mg, 1.04 mmol) and pyridine (307.1 mg, 3.88 mmol) are added to a solution of 13 (384.4 mg, 1.55 mmol) in chloroform (30 mL) and the mixture is stirred at room temperature for 3 hours. Compound 4 (942.8 mg, 3.88 mmol) and DMAP (474 mg, 3.88 mmol) are added to the solution of isothiocyanate, 24, and the mixture is stirred at 35–40° C. overnight. The reaction solution is washed with 0.5 N HCl (3×10 mL), water (10 mL) and dried over anhyd $MgSO_4$, followed by removal of the solvent in vacuo. The residue is purified by silica gel column chromatography (0→20% MeOH in $CHCl_3$) to give product.

Example 18

TFA salt of thiourea derivative of ara-C: Compound (26). Compound 25 is subjected to the conditions as described for the preparation of 6 to give 26.

Example 19

20-O-[(2-aminoethoxy)-ethoxy]-acetic acid carbonate derivative of camptothecin TFA salt (30).

A suspension of camptothecin (27, 139 mg, 0.40 mmol), trophosgene (44 mg, 0.147 mmol) and DAMP (156 mg, 1.28 mmol) in anhydrous DCM (20 mL) is stirred for 10 minutes to form 28. Compound 2 (82 mg, 0.40 mmol) is added and the reaction mixture stirred for 16 hours, followed by removal of the solvent in vacuo. The residue is recrystallized from DCM-ether to give 29. Compound 29 is subjected to the condition as described for the preparation of 6 to give 30.

Example 20

PEG-spacer-drug derivatives. (33A-G)
33A: Method A-from T-PEG

A mixture of 6 (200 mg, 0.53 mmol), T-PEG 40,000, see Greenwald, R. B., et al., "PEG Thiazolidine-2-Thione. A Novel Reagent For Facile Protein Modification Of Bovine Hemoglobin", *Bioconjugate Chem.* 1996, 7, 638–641, the contents of which are incorporated herein by reference, (31, 2.0 g, 0.050 mmol), and DIEA (300 μL, 1.73 mmol) in DMF (15 mL) and DCM (15 mL) was stirred at room temperature overnight. The solvent was removed in vacuo and the residue was recrystallized from IPA to give 1.7 g (85%) of product. The amount of ara-C present in this compound as measured by UV assay was 1.05% and the conjugation (PEG conversion) yield 88%: $^{13}C$ NMR δ 37.50, 59.55, 60.83, 63.89, 67.51–70.51 (PEG), 74.11, 85.02, 86.96, 92.81, 145.28, 151.67, 154.19, 161.40, 169.18.

33A: Method A-from PEG-acid.

EDC.HCl (380.7 mg, 1.98 mmol) is added to a mixture of PEG-acid 40,000 (32, 10.0 g, 0.24 mmol), 6 (468 mg, 1.24 mmol), and DMAP (486 mg, 3.97 mmol) in anhydrous DCM (100 mL) and DMF (50 mL) at 0° C. and the mixture is slowly warmed to room temperature overnight. The solvent is removed and the residue recrystallized from IPA to give product.

33B-G: Compound 12, 16, 20, 23, 26, and 30 are each treated with the conditions as described the preparation of 33A.

Example 21

In vitro experiment.

Cell Lines and Cytotoxicity Assays. Studies using P388/0 cell lines for $IC_{50}$ (drug concentration inhibiting growth of cells by 50%) were maintained and conducted using standard procedures. Briefly, for $IC_{50}$ determination, cells were seeded into the microwell plates at a density of $2\times10^3$ cells per 50 μL per well. Plates were incubated at 37° C. in a humidified incubator with 5% $CO_2$ for 3 days. Cell growth was measured by the addition of 10 μL/well of Alamar Blue (Alamar Biosciences, Inc., Sacramento, Calif.) and the plates were incubated a further 4 hours at 37° C. The $IC_{50}$ values for each compound were determined from absorbance versus dilution factor plots. All cell cultures for animal implantation were maintained at 37° C. in a humidified atmosphere of 5% $CO_2$/95% $O_2$ and subcultured once a week. All cell lines were periodically tested for Mycoplasma and were Mycoplasma free. The results are shown in Table 1.

TABLE 1

| In vitro result of Ara-C and the PEG Derivative. | |
|---|---|
| Compound | $IC_{50}$ (P388/0, nM) |
| Ara-C | 10 |
| 33A | 226 |

G. References

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the formula:

wherein:

G is a linear or branched polymer residue;

$Y_1$ and $Y_2$ are independently O, S, or $NR_9$;

$M_1$–$M_3$ are independently O, S, or $NR_{10}$;

$M_4$ is X or Q;

wherein X is an electron withdrawing group and Q is a moiety containing a free electron pair positioned three to six atoms from $C(=Y_2)$;

B is a residue of an amine-containing moiety or a residue of a hydroxyl-containing moiety;

$R_{1-10}$ are independently selected from the group consisting of hydrogen, $C_{1-6}$ alkyls, $C_{3-12}$ branched alkyls, $C_{3-8}$ cycloalkyls, $C_{1-4}$ substituted alkyls, $C_{3-8}$ substituted cycloalkyls, aryls, substituted aryls, aralkyls, $C_{1-4}$ heteroalkyls and substituted $C_{1-4}$ heteroalkyls;

a, b, c, d, h, i and n ore each independently zero or a positive integer; and e, f and g are each independently a positive integer.

2. The compound of claim 1, wherein G includes a capping group A, selected from the group consisting of hydrogen, $CO_2H$, $C_{1-6}$ alkyl moieties, and (II')

3. A compound of claim 2, of the formula:

(II)

4. The compound of claim 1, wherein a, b, c, d, h, i and n are independently zero, one or two.

5. The compound of claim 1, wherein $Y_1$ and $Y_2$ are both O.

6. The compound of claim 1, wherein $M_2$ is NH and d is one.

7. The compound of claim 1, wherein $R_7$ and $R_8$ are both H.

8. The compound of claim 1, wherein n is 1.

9. The compound of claim 1, wherein a is 0.

10. The compound of claim 1, wherein a is 1.

11. The compound of claim 1, wherein c is 0.

12. The compound of claim 1, wherein g is 2, $M_3$ is O, e is 2, f is 1 and $R_3$ and $R_4$ are H.

13. The compound of claim 12, wherein b, d, h and n are 1, $R_5$ and $R_6$ are H and $M_2$ is NH.

14. The compound of claim 12, wherein b, d and n are 1, $M_2$ is NH and $R_3$ and $R_4$ are H.

15. The compound of claim 1, wherein B is a residue of an amine-containing moiety.

16. The compound of claim 15, wherein said amine-containing moiety is wherein $R_{12-13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls, substituted $C_{1-6}$ heteroalkyls;

$R_{14-18}$ are independently selected from alkoxy, e.g. $OR_{19}$ or, in the alternative, H, OH, $N_3$, $NHR_{20}$, $NO_2$ or CN, fluoro, chloro, bromo, iodo, where $R_{19-20}$ are independently selected from the same group which defines $R_{12-13}$.

17. The compound of claim 1, wherein G is O—$(CH_2CH_2O)_x$ or O—$(CH(CH_3)CH_2O)_x$, wherein x is the degree of polymerization.

18. The compound of claim 17, wherein G is O—$(CH_2CH_2O)_x$ and x is a positive integer selected so that the weight average molecular weight is at least about 20,000.

19. The compound of claim 18, wherein G has a weight average molecular weight of from about 20,000 to about 100,000.

20. The compound of claim 19, wherein G has a weight average molecular weight of from about 25,000 to about 60,000.

21. A compound of claim 1, selected from the group consisting of:

-continued and

22. A compound of claim 3, selected from the group consisting of:

23. A compound of claim 1, selected from the group consisting of:

24. A compound of claim 3, selected from the group consisting of:

25. A method of preparing a polymeric conjugate, comprising:

a) reacting a biologically active moiety having an unprotected amine or hydroxyl group with a compound of the formula (III)

wherein $B_1$ is a leaving group capable of reacting with an unprotected amine or hydroxyl group;

$B_2$ is a cleavable protecting group;

$Y_2$ is O, S, or $NR_9$;

$M_2$–$M_3$ are independently O, S, or $NR_{10}$;

$M_4$ is X or Q;

wherein X is an electron withdrawing group and Q is a moiety containing a free electron pair positioned three to six atoms from C(=$Y_3$);

$R_{3-6}$, $R_9$ and $R_{10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

d, h, and i are each independently zero or a positive integer; and e, f and g are each independently a positive integer to form a protected intermediate of the formula:

(IV)

wherein

B is a residue of an amine-containing moiety a residue of a hydroxyl-containing moiety;

b) deprotecting the resultant intermediate by removing $B_2$; and c) reacting the deprotected intermediate with a compound of the formula wherein $B_3$ is a leaving group;

G is a polymer residue;

$Y_1$ is O, S, or $NR_9$;

$M_1$ is O, S, or $NR_{10}$;

$R_1$, $R_2$, $R_7$, $R_9$ and $R_{10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; and a, b and c are each independently zero or a positive integer, whereby a polymeric conjugate is formed.

26. A method of preparing a polymeric conjugate, comprising:

reacting a polymer-spacer intermediate of the formula wherein
- $B_1$ is a leaving group capable of reacting with an unprotected amine or hydroxyl group;
- G is a polymer residue;
- $Y_1$ and $Y_2$ are independently O, S, or $NR_9$;
- $M_1$–$M_3$ are independently O, S, or $NR_{10}$;
- $M_4$ is X or Q;
- wherein X is an electron withdrawing group and Q is a moiety containing a free electron pair positioned three to six atoms from $C(=Y_2)$;
- B is a residue of an amine-containing moiety or a residue of a hydroxyl-containing moiety;
- $R_{1-10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;
- a, b, c, d, h, i and n are each independently zero or a positive integer; and
- e, f and g are each independently a positive integer;

and thereafter reacting intermediate with a biologically active moiety having an unprotected amine or hydroxyl group to form the polymeric conjugate.

27. A method of treatment, comprising:

administering to a mammal in need of such treatment an effective amount of a compound of claim 1, wherein B is a residue of a biologically active moiety.

28. A method of treatment, comprising:

administering to a mammal in need of such treatment an effective amount of a compound of claim 3, wherein B is a residue of a biologically active moiety.

29. A compound of the formula:

(IV)

wherein
- B is a residue of an amine-containing moiety or a residue of a hydroxyl-containing moiety;
- $B_2$ is a cleavable protecting group;
- $Y_2$ is O, S, or $NR_9$;
- $M_2$–$M_4$ are independently O, S, or $NR_{10}$,
- $M_4$ is X or Q;

wherein X is an electron withdrawing group and Q is a moiety containing a free electron pair positioned three to six atoms from $C(=Y_2)$;

(V')

- $R_{3-6, 9\ and\ 10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;
- d, e, f, g, h, and i are each independently zero or a positive integer.

30. A compound of claim 1, selected from the group consisting of:

and

31. A compound of claim 3, selected from the group consisting of:

and

32. The compound of claim 1, wherein e, f and g are each independently one or two.

* * * * *

UNITED STATES PATENT AND TRADEMARK OFFICE
CERTIFICATE OF CORRECTION

PATENT NO. : 6,756,037 B2
DATED : June 29, 2004
INVENTOR(S) : Greenwald, R.B. et al.

It is certified that error appears in the above-identified patent and that said Letters Patent is hereby corrected as shown below:

Column 21,
Lines 11 and 12, "C1-4" should read -- C1-6 --;
Line 14, "ore" should read -- are --;

Column 25,
Line 57, "Y3" should read -- Y2 --; and

Column 26,
Line 53, the following formula (V) should appear below the word "wherein" and above the phrase "B3 is a leaving group".

Signed and Sealed this

Eighth Day of February, 2005

JON W. DUDAS
*Director of the United States Patent and Trademark Office*